United States Patent [19]

Ueno

[11] 4,441,982

[45] Apr. 10, 1984

[54] COMBUSTION SENSING APPARATUS

[75] Inventor: Sadayasu Ueno, Katsuta, Japan

[73] Assignee: Hitachi, Ltd., Tokyo, Japan

[21] Appl. No.: 377,411

[22] Filed: May 12, 1982

[30] Foreign Application Priority Data

May 15, 1981 [JP] Japan .................................. 56-72352

[51] Int. Cl.³ ........................ G01N 27/58; F23N 5/00
[52] U.S. Cl. .................................... 204/426; 204/428;
204/425; 204/424; 204/1 T; 422/94; 431/76
[58] Field of Search ............... 204/195 S, 1 S, 421,
204/427, 428, 426, 425, 424; 431/76, 116, 75;
422/94

[56] References Cited

U.S. PATENT DOCUMENTS

| | | | |
|---|---|---|---|
| 4,049,503 | 9/1977 | Becker et al. .................. | 204/195 S |
| 4,088,543 | 5/1978 | Ruka ............................. | 204/1 S |
| 4,240,891 | 12/1980 | Bannister ...................... | 204/1 S |
| 4,272,350 | 6/1981 | Croset et al. .................. | 204/195 S |
| 4,304,652 | 12/1981 | Chiba et al. ................... | 204/195 S |
| 4,359,030 | 11/1982 | Sone et al. .................... | 204/195 S |
| 4,395,226 | 7/1983 | Nakanishi et al. ............. | 431/76 |

Primary Examiner—John F. Niebling
Assistant Examiner—B. J. Boggs, Jr.
Attorney, Agent, or Firm—Antonelli, Terry & Wands

[57] ABSTRACT

A combustion sensing apparatus having a solid electrolyte disposed in the vicinity of a burner and having a tabular form. Thanks to the tabular form of the solid electrolyte, the production of the apparatus is very much facilitated and the areas occupied by the anode and cathode are minimized. The construction of the apparatus as a whole is simplified and the reliability of the same is improved remarkably. In addition, the cost of production is lowered advantageously.

5 Claims, 6 Drawing Figures

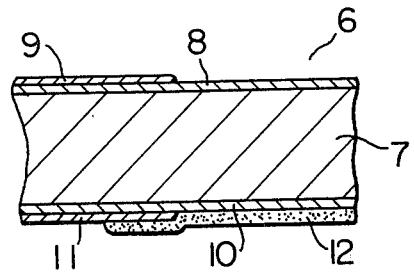
FIG. 3
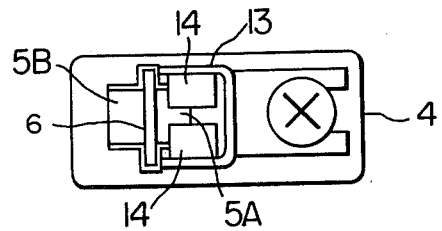
FIG. 4
FIG. 5
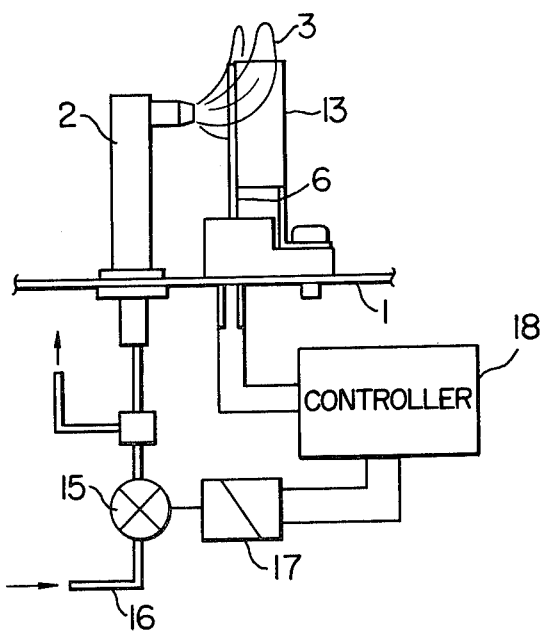

COMBUSTION SENSING APPARATUS

BACKGROUND OF THE INVENTION

The present invention relates to a combustion sensing apparatus having an air fuel ratio sensor incorporating a solid electrolyte such as stabilized zirconia and suited for use in the detection of oxygen concentration in a flame.

In the use of combustion sensor, it is necessary to expose the cathode and anode formed on a solid electrolyte separately to the atmosphere as a reference gas and to the gas to be measured, respectively. In order to make sure of the separation, the solid electrolyte is shaped in a tubular form opened at its both ends of closed only at one end thereof.

The work for forming an anode on the inner surface of such a tubular combustion sensor has to be conducted manually, regardless of whether the tubular body of the sensor is closed at its one end or opened at its both ends. In addition, the contruction of the lead from the electrode is complicated. For these reasons, the cost of production is raised uneconomically and the reliability is deteriorated undesirably.

In the case of the air-fuel ratio sensor, the cathode and anode are produced in the form of porous films, and the catalytic action performed by the porous films largely affects the output characteristics of the sensor. Therefore, a severe control is necessary for the control of the porosity, thickness and other factors of the anode formed on the inner peripheral surface of the cylindrical sensor body. Actually, however, the major portion of the anode cannot be checked visually. This imposes various problems.

The production cost is ruled also by the amount of platinum or the like precious metal alloy used as the material of the electrodes formed on the inner and outer surface of the solid electrolyte tube. Although effort is concentrated to reduce the amount of use of such a precious metal alloy, as a matter of fact, the formation of the electrodes is very difficult so that the alloy is wastefully consumed to form the electrode or leads covering unnecessarily large area, resulting in a raised cost of production.

SUMMARY OF THE INVENTION

Accordingly, an object of the invention is to provide a simple and reliable combustion sensing apparatus.

To this end, according to the invention, there is provided a combustion sensing apparatus comprising a cathode disposed in the vicinity of a burner and formed on the surface of a solid electrolyte subjected to the flow of hot exhaust gas, and an anode formed on the surface of the solid electrolyte subjected to an atmosphere of a reference gas, wherein the improvement comprises that the solid electrolyte is shaped to have a tabular form.

BRIEF DESCRIPTION OF THE DRAWINGS

FIG. 3 is a sectional view taken along the line III—III of FIG. 2a;

FIG. 4 is a plan view of the combustion sensor; and

FIG. 5 is a circuit diagram of a circuit connected to the combustion sensor.

DESCRIPTION OF THE PREFERRED EMBODIMENT

The invention will be fully understood from the following description of the preferred embodiment.

Figure 1:
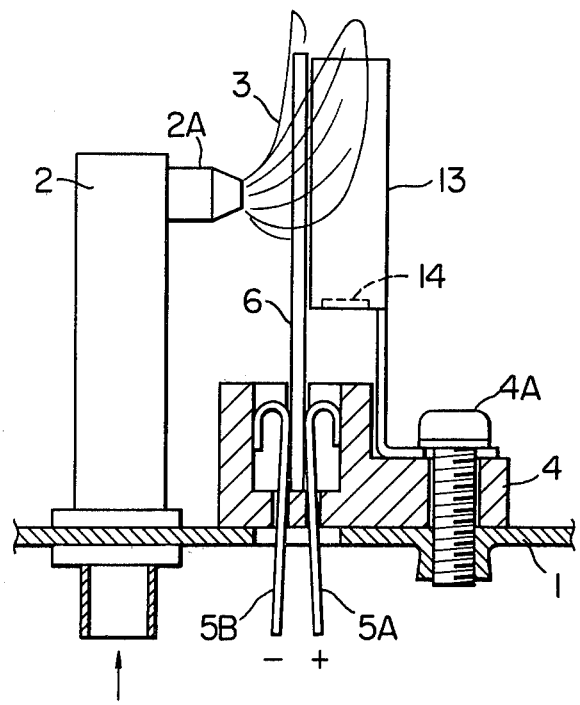
FIG. 1 is a partly sectioned side elevational view of the combustion sensor constructed in accordance with an embodiment of the invention.

Referring first to FIG. 1 showing particularly the combustion sensing section of a combustion sensing apparatus in accordance with the invention, a pilot burner 2 mounted on a base 1 is adapted to be supplied with a fuel from the lower side of the base 1. The pilot burner 2 has a nozzle 2A extending in parallel with the base 1 and adapted to jet a flame 3. A socket 4 is fixed by a screw 4A to the portion of the base 1 in front of the nozzle 2A. The socket 4 has a pair of electrodes 5A and 5B biased toward each other and led to the lower side of the base 1. A sensor element 6 is clamped between the electrodes 5A and 5B of the socket 4. The sensor element 6 has a tabular form and is disposed such that the upper portion of one side of the sensor element 6 is contacted by the flame jetted from the nozzle 2A. In consequence, the sensor element 6 is heated up to an operating temperature ranging between 300° and 1000° C.

Figure 2A:
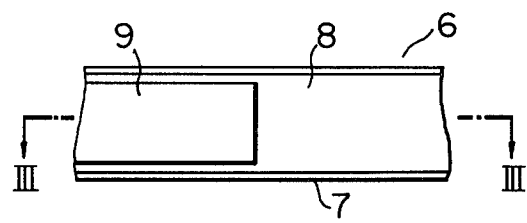
FIGS. 2a and 2b are side elevational views as viewed from both sides of an example of a sensor element.
Figure 2B:
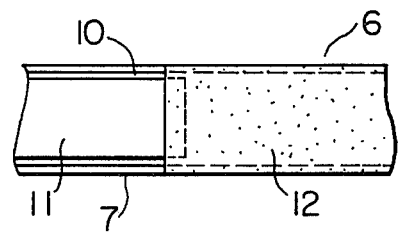

As will be seen from FIGS. 2a and 2b, the sensor element 6 has a substrate 7 having a tabular form and made from a solid electrolytic material, such as stabilized zirconia, and is covered at its one side by an anode plate 8 as shown in FIG. 2a. The anode plate 8 consists of a porous film of, for example, platinum and is formed by vacuum evaporation or the like method. The anode plate 8 is provided at its one end with an anode lead plate 9 made of a material which serves merely as an electrically conductive body. For instance, this lead plate 9 can be formed by applying and firing platinum paste. On the other side of the substrate 7, a cathode plate 10 and a cathode lead 11 are formed in the same manner as the opposite side, as will be seen from FIG. 2a. A protective film 12 is formed to cover the major part of the cathode plate 10 connected to the cathode lead 11. The protective film 12 is a porous film so that it can function also as a catalyst while serving as a protector for preventing the cathode plate 10 from being contacted directly by the flame 3. The sensor element 6 shown in FIG. 2a has a sectional shape as shown in FIG. 3 which is a sectional view taken along the line III—III of FIG. 2a.

Referring back to FIG. 1, the sensor element 6 is arranged such that the protective film 12 faces the nozzle 2A and is contacted at its anode lead plate 9 and cathode lead plate 11 by the electrodes 5A and 5B, respectively.

A shielding member 13 is disposed at the rear side of the sensor element 6. As will be seen from FIG. 4, the shielding member 13 is composed of a substantially U-shaped member turned sideways, so that a space is formed between the shielding member 13 and the sensor element 6 for permitting air to flow therein in the vertical direction. The shielding member is supported by the screw 4A for fixing the socket 4 to the base 1. The shielding member 13 effectively prevents the flame 3 from stretching behind the sensor element, i.e. to the same side as the anode. An upward flow of air is produced due to a convection caused by the heat, in the space adjacent to the anode and surrounded by the shielding member 13. This air contains about 20% of oxygen and serves as the reference gas in relation to the hot combustion gas which flows at the same side as the cathode. Blades 14 provided at the inner side of lower end of the shielding member 13 restrict the flow of air, thereby to prevent excessive cooling of the sensor element by the flow of air.

As will be seen from FIG. 5, the pilot burner 2 is adapted to be supplied with fuel through a main pipe 16 via a solenoid valve 15. This main pipe 16 is branched at the downstream side of the solenoid valve 15 into two pipes one of which leads to the pilot burner 12 while the other leads to a main burner. The solenoid valve 15 is adapted to be actuated to open and close by a solenoid coil 17 which is under the control of the output from a controller 18 adapted to operate in response to the output from the sensor element 6.

For instance, when the mixture is too rich, i.e. the oxygen content is too small, the sensor element 6 produces an electromotive power of 0.5 to 0.8 V which serves to operate the controller 18 thereby to close the solenoid valve 15. On the other hand, when the fire on the pilot burner 2 is put off, the sensor element 6 is not heated so that the internal resistance, which is 1 K$\Omega$ or less before the heating, is drastically increased to 10 M$\Omega$ or higher. Upon detect of the increase of the resistance, the controller 18 operates to close the solenoid valve 15.

In the described embodiment of the invention, the formation of the anode and cathode on both sides of the sensor element 6 can be made in quite an easy manner by a known method such as evaporation or printing, thanks to the tabular form of the sensor element. Most conveniently, the solid electrolyte, as the substrate, is formed by, for example, rolling in a tabular form having a large area and, after forming the electrodes on respective surfaces, cut into independent sensor elements by means of a laser scriber or a diamond cutter.

In addition, the tabular form of the sensor element 6 affords an easy visual check of the anode and cathode which in turn permits an easier control of the porosity, thickness and other factors of the anode and cathode.

Furthermore, since a sufficiently large space is preserved above the region in which the electrode is to be formed, it is possible to form the electrode precisely on the required region to eliminate wasteful use of the precious metal alloy, thereby to lower the cost of production.

The separation of reference gas and the atmosphere from each other can be made at a high reliability because the stretching of the flame 3 into the anode side is avoided by the presence of the shielding member 13.

In the described embodiment of the invention, the extension of the flame into the anode side, which may occur due to the tabular form of the sensor element 6, is prevented by the shielding member 13. The shielding member, however, is not essential and may be dispensed with provided that the flame 3 does not have such an intensity as to extend behind the sensor element 6.

In the described embodiment, the anode is formed on one side of the solid electrolyte while the cathode is formed on the other side of the latter. This arrangement, however, is not always necessary. Namely, in the case where the shielding member 13 can be neglected, it is possible to arrange such that the cathode and the anode are formed on the same side of the solid electrolyte separately from each other and disposed at portions contactable and not contactable with the flame, respectively.

As has been described, according to the invention, it is possible to obtain a combustion sensing apparatus having a simplified construction and operable at a high reliability.

Although the invention has been described through a specific embodiment, it is to be noted that the described embodiment is not exclusive and various changes and modifications may be imparted thereto without departing from the scope of the invention which is limited solely by the appended claims.

What is claimed is:

1. A combustion sensing apparatus comprising a combustion sensor disposed in the vicinity of a burner and a flame jetted thereby, said combustion sensor being formed of a solid electrolyte having a cathode formed on a surface of the solid electrolyte that is oriented so as to be subjected to the flow of a hot combustion gas produced in the vicinity of said flame, and an anode formed on a surface of said solid electrolyte subjected to an atmosphere of a reference gas, characterized in that said solid electrolyte has a tabular form and is provided with said anode and cathode on opposite surfaces of a free end thereof, said apparatus further having a shielding member mounted to a support means so as to be positioned adjacent the side of the free end of the solid electrolyte upon which said anode is formed in a manner so as to prevent the flame jetted from said burner from extending to the same side of said solid electrolyte as said anode.

2. A combustion sensing apparatus according to claim 1, wherein said shielding member has a channel-like portion of substantially U-shaped cross section disposed in a parallel relationship to a longitudinal direction of said tabular solid electrolyte so as to create a reference air flow space along the anode side of said solid electrolyte.

3. A combustion sensing apparatus according to claim 2, wherein said channel-like portion of the shielding member has a flow restricting means at an air in-flow end of said reference air flow space.

4. A combustion sensing apparatus according to claim 3, wherein said flow restricting means comprises blades projecting transversely inwardly from an in-flow end of opposite sides of said U-shaped cross section.

5. A combustion sensing apparatus according to claim 1, wherein said burner and said support means are mounted to a base, and wherein said support means is a socket-like part having a recess within which a pair of electrodes are biased together so as to clamp an end of the combustion sensor therebetween.

* * * * *